US012527557B2

(12) United States Patent
Rackers et al.

(10) Patent No.: US 12,527,557 B2
(45) Date of Patent: Jan. 20, 2026

(54) BIOPSY NEEDLE SET WITH REDUCED DEFLECTION AND IMPROVED TARGETING

(71) Applicant: URO-1, Inc., Greensboro, NC (US)

(72) Inventors: Kevin Rackers, Greensboro, NC (US); Philip M. Allred, III, Kernersville, NC (US); Jack Snoke, Winston Salem, NC (US); Ted Belleza, La Selva Beach, CA (US); Bela Denes, Jacksonville, OR (US)

(73) Assignee: URO-1, Inc., Winston-Salem, NC (US)

( * ) Notice: Subject to any disclaimer, the term of this patent is extended or adjusted under 35 U.S.C. 154(b) by 0 days.

(21) Appl. No.: 18/581,296

(22) Filed: Feb. 19, 2024

(65) Prior Publication Data

US 2024/0252156 A1 Aug. 1, 2024

Related U.S. Application Data

(63) Continuation-in-part of application No. 17/082,387, filed on Oct. 28, 2020, now Pat. No. 11,903,569, and a continuation-in-part of application No. 18/119,042, filed on Mar. 8, 2023.

(60) Provisional application No. 63/630,443, filed on Feb. 5, 2024.

(51) Int. Cl.
*A61B 10/02* (2006.01)

(52) U.S. Cl.
CPC ................................ *A61B 10/0275* (2013.01)

(58) Field of Classification Search
CPC ........................ A61B 10/0275; A61B 10/0241
See application file for complete search history.

(56) References Cited

U.S. PATENT DOCUMENTS 4,733,662 A * 3/1988 DeSatnick ..... A61B 17/320016 30/162
8,882,681 B2 * 11/2014 Neoh ................ A61B 10/0275 600/566
9,149,260 B2 10/2015 Stone
10,188,422 B2 1/2019 Stone
10,478,159 B2 11/2019 Stone
2012/0022397 A1 * 1/2012 Jarial ................ A61B 10/0275 600/567
2013/0030323 A1 * 1/2013 Smith ................ A61B 10/0275 600/567

(Continued)

FOREIGN PATENT DOCUMENTS

EP 0221007 A1 * 5/1987 ......... A61B 10/0283

*Primary Examiner* — Rene T Towa
(74) *Attorney, Agent, or Firm* — Wissing Miller LLP

(57) ABSTRACT

A biopsy needle set includes a biopsy needle with a tip that terminates distally in a laterally extending cutting edge that is spaced up from the bottom surface of the needle. A cradle, proximal to the needle, has a floor that is below a central axis of the needle and a row of teeth upwardly extending up from each lateral side of the floor up to about the central axis. Within each row, the teeth are distant from each other and the teeth of the two rows are staggered such that some cross-sections of the cradle include only one tooth and some none. The outer surface of the cradle bears against the inner surface of the cannula to keep the biopsy needle centered in the cannula and from bending to thereby better target tissue of interest for sampling.

16 Claims, 7 Drawing Sheets

(56) References Cited

U.S. PATENT DOCUMENTS

| | | | | |
|---|---|---|---|---|
| 2014/0277040 | A1* | 9/2014 | Hayes | A61B 17/32002 606/170 |
| 2017/0340352 | A1* | 11/2017 | Stone | A61B 17/3417 |

* cited by examiner

100

100

BIOPSY NEEDLE SET WITH REDUCED DEFLECTION AND IMPROVED TARGETING

REFERENCE TO RELATED APPLICATIONS

This application claims the benefit of and incorporates by reference U.S. Provisional Application No. 63/630,443 filed on Feb. 5, 2024.

This application is a continuation in-part of and incorporates by reference each of (1) U.S. patent application Ser. No. 17/082,387 filed Oct. 28, 2020 (scheduled to issue as U.S. Pat. No. 11,903,569 on Feb. 20, 2024), and (2) U.S. patent application Ser. No. 18/119,042 filed Mar. 8, 2023.

FIELD

This patent specification relates to biopsy devices and methods, including but not limited to devices for taking tissue samples of prostate tissue.

BACKGROUND

Notched biopsy needle sets have long been used to take samples of tissue. A standard-of-care (SOC) needle set comprises a needle, sometimes called a stylet or core collector, that has a pointed tip designed to penetrate tissue, followed proximally by a notch into which surrounding tissue can protrude, and a shaft. The needle set further includes a cutting cannula that slides coaxially around the needle and has a sharp distal edge. The needle set can be used with a completely manual instrument with which a health professional manually pushes the needle into tissue until the notch is in tissue of interest and then manually pushes the cannula over the needle toward the needle tip to cut tissue that has entered the notch and to contain in in the notch while withdrawing the needle set from the tissue. With a semi-automated instrument, the practitioner manually drives the needle into tissue the same way but thereafter releases a spring-loaded cutting cannula to cut and contain the tissue sample. A fully automated instrument spring-loads both the needle and the cannula. The health professional inserts the needle with the cannula covering the notch in the patient until the needle tip is near or in target tissue and then releases the needle to shoot distally into the tissue to be sampled. The spring-loaded cutting cannula then shoots distally to cut off and contain the sample in the notch and then withdraws the needle set from the patient and pulls the cannula back to expose and retrieve the tissue sample from the needle notch for initial assessment and/or for shipping to a pathology laboratory.

One of the important needs in such procedures is to obtain tissue samples that are as large in volume, cross-section and length as possible given the cross-section of the needle set and as intact as possible so that they would faithfully represent the tissue from which they were severed. Another is to keep the biopsy needle from bending at the thinner, notched portion thereof and missing intended target tissue and/or otherwise disturbing live tissue.

This patent specification is directed to devices and methods toward meeting such needs and other needs and providing other improvements in biopsy needle sets and related methods.

SUMMARY

According to some embodiments, a biopsy needle set comprises a biopsy needle that extends along a central axis that is at a level midway between a top extent and a bottom extent of the needle, wherein said needle comprises: a tip, a cradle proximal to the tip, and a shaft proximal to the cradle, wherein; the tip comprises upper and lower facets that converge to each other in a distal direction to form a distal cutting edge that is at the distal end of the tip and extends in a lateral direction; the cradle comprises an upwardly facing floor that is between said central axis and the bottom extent of the needle, has lateral sides flanking the central axis, and a row of teeth that extend up from each lateral side of said floor to a level approximating that of the central axis, wherein the teeth of each row are spaced from each other along the central axis; and said laterally extending, distal cutting edge is spaced up from said bottom extent of the needle but is below the level of said floor of the cradle.

According to some embodiments, the biopsy needle set can further include one or more of the following: (a) the distal cutting edge can be at a level spaced up from the bottom extent of the needle by a distance approximating a third of the distance from the bottom extent of the needle to the level of the floor of the cradle; (b) the distal cutting edge can be at a level spaced up from the bottom extent of the needle by 15 thousands of an inch plus or minus 5 thousands of an inch; (c) said upper and lower facets can comprise two lower facets that are side-by-side; (d) said lower facets can comprise two lower facets that converge to an up-down edge that is below and extends proximally from the laterally extending cutting edge; (e) said upper and lower facets can comprise two lower facets each of which is shorter along the central axis than the upper facet; (f) the teeth can be arranged such that some cross-sections of the cradle include only one of said teeth and some do not include any of said teeth; (g) said laterally extending distal cutting edge can be V-shaped in top view; (h) said laterally extending distal cutting edge can comprise two portions each extending along a respective straight line; (i) said laterally extending distal cutting edge can extend along a single straight line; (j) said laterally extending distal cutting edge can extend along at least one curved line; and (k) the set can further comprise a hollow cutting cannula configured to slide distally and proximally over the biopsy needle along the central axis such that an outside bottom surface of the cradle and outside surface of the teeth bear against and inner surface of the cannula to keep the needle centered in the cannula to resist bending of the needle when a part of the cradle extends distally out of the cannula.

DETAILED DESCRIPTION

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some or all these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features of other described embodiments or with other features. Like reference numbers and designations in the various drawings indicate like elements.

Figure 1:
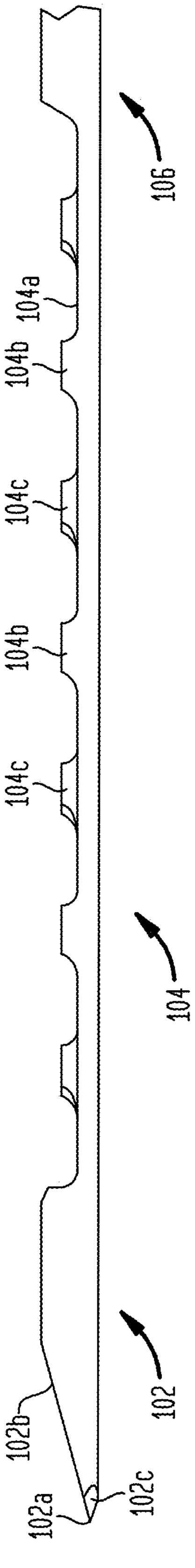
FIG. 1 is a left side view of a distal portion of a biopsy needle according to some embodiments.
Figure 2:
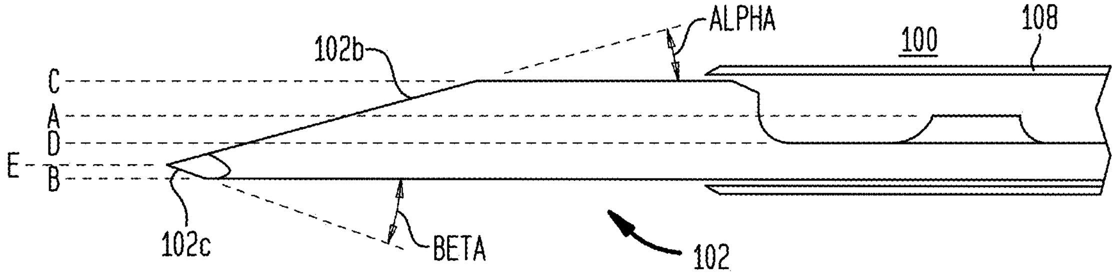
FIG. 2 is a left side enlarged view of a distal portion of the biopsy needle, according to some embodiments.

FIG. 1 is a left side view of a portion of a biopsy needle 100 and FIG. 2 is an enlarged view of a distal portion of the biopsy needle, according to some embodiments. The needle extends along a central axis A and includes tip 102, cradle 104 proximal to the tip, and shaft 106 proximal to the cradle. Central axis A is at the center of a cross-section through shaft 106. The bottom extent of needle 100 is at level B and the top extent of needle 100 is at level C. Shaft 106 has a portion (not shown in FIGS. 1 and 2)) that extends further to the right in FIGS. 1 and 2 and has a proximal end configured for attachment, fixed or removable, to an instrument not shown in FIGS. 1 and 2 but described infra. Biopsy needle 100 typically is a part of a biopsy needle set that further includes a cutting cannula 108. A proximal portion of cannula 108 is seen in FIG. 2. Cutting cannula 108 has a sharp distal end 108*a* and is configured to slide distally and proximally while surrounding biopsy needle 100. Cannula 108 has a portion (not shown in FIG. 2) that extends further to the right and is configured for attachment to an instrument as described infra.

It should be clear that positional terms such as upper, lower, above, below, etc. refer to the orientation of biopsy needle 100 illustrated in FIGS. 1 and 2 and that different orientations of needle 100 relative to an observer would require adapting these positional terms accordingly.

Figure 3:
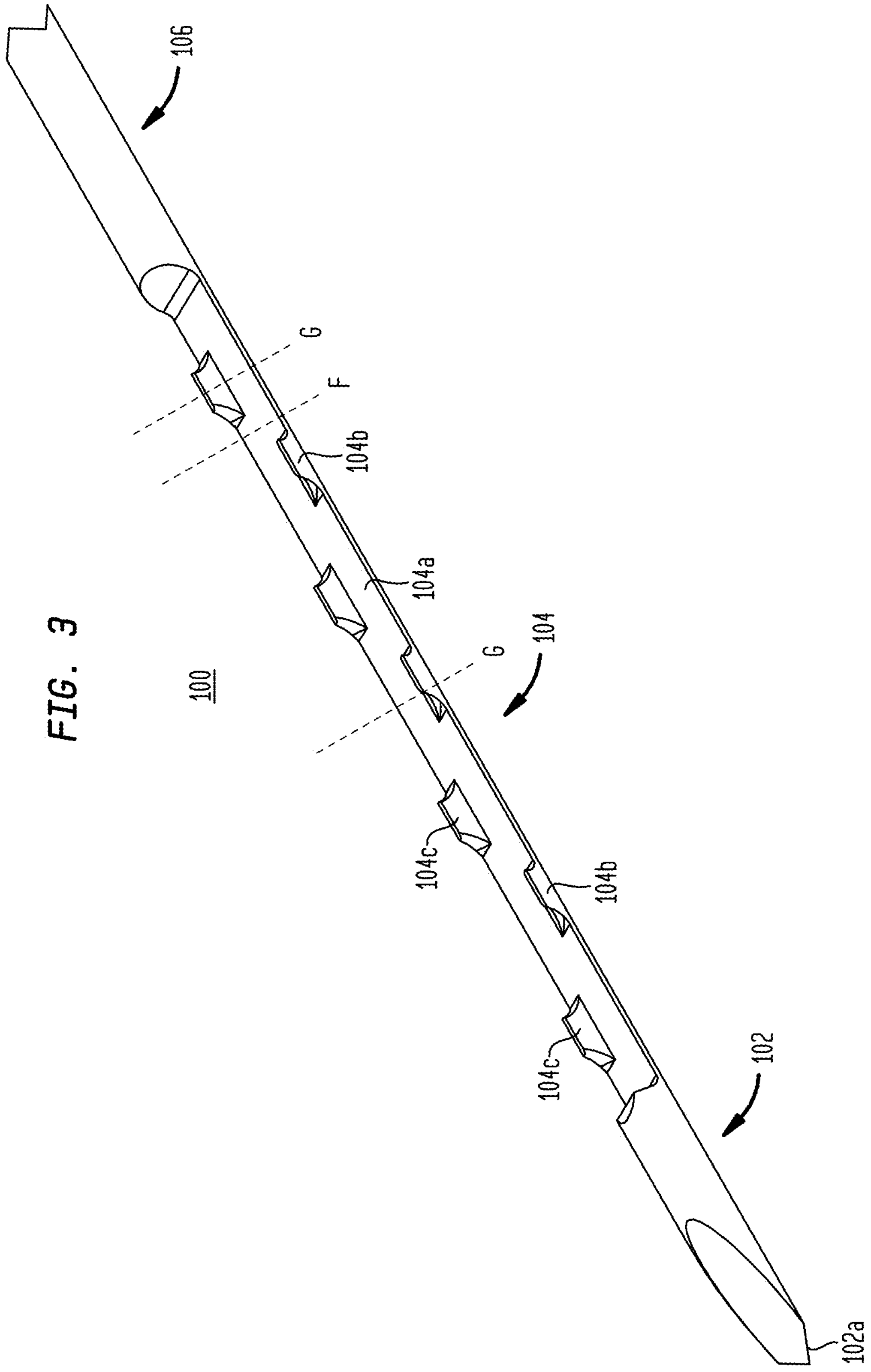
FIG. 3 is a perspective view of a distal portion of a biopsy needle, from a viewpoint to the left of the needle, according to some embodiments.

FIG. 3 is a perspective view of a distal portion of biopsy needle 100, from a viewpoint to the left of the needle, according to some embodiments, and illustrates an upwardly facing floor 104*a* of cradle 104, a left row of teeth 104*b* extending up from a left side of floor 104*a* and a right row of teeth 104*c* extending up from a right side of floor 104*a*. As seen in FIG. 2, floor 104*a* is at a level D that is below central axis A. Teeth 104*b* extend up to, or approximately to, the level of central axis A, i.e., to or approximately to half the diameter of biopsy needle 100 in cross-section of shaft 106, as do teeth 104*c*. Teeth 104*b*, in the left row of teeth, are spaced axially from each other. Teeth 104*c*, in the right row of teeth, also are spaced axially from each other. For example, the teeth in a row can be spaced axially as illustrated in FIG. 1, scaled to the dimensions of a specific biopsy needle. In the example of FIG. 1, each tooth is spaced from an adjacent tooth in the same row by 2-3 times the axial length of a tooth at the level of cradle floor 104*a*. In this example, the most distal tooth is spaced from tip 102 by at least the axial length of one tooth and the most proximal tooth is spaced from shaft 106 by at least the axial length of a tooth. As an example, for a cradle 104 that is 20 mm in axial length, one row can have 3 teeth and the other 4 teeth.

Preferably, the teeth of the left and right rows are staggered such that some cross-sections through cradle 104, such as sections F, include a tooth such as 104*b* or 104*c*, but some sections such as G do not include any such teeth. For example, a cross-section such as G includes no structure above cradle floor 104*a*.

An important feature of biopsy needle 100 is the shape of the distal portion of tip 102, including how that distal cutting edge 102*a* is raised above the level B of the bottom extent of biopsy needle 100 and how this cutting edge 102*a* is elongated in a direction parallel to or generally parallel to cradle floor 104*a* (which can be flat or curved such as somewhat concave or convex).

As seen in FIG. 2, tip 102 terminates distally in a sharp distal cutting edge 102*a* formed at the convergence of upper and lower facets 102*b* and 102*c*. Cutting edge 102*a* is at a level E that is up from the level B of the bottom extent of needle 100 but is below the level D of floor 104*a* cradle 104. Level E of cutting edge 102*a* preferably is up from level B by about a third of the distance between levels B and D, but this can vary somewhat. In a specific example, the distance is 15 thousands of an inch, or is that distance plus or minus 5 thousands of an inch.

Figure 4:
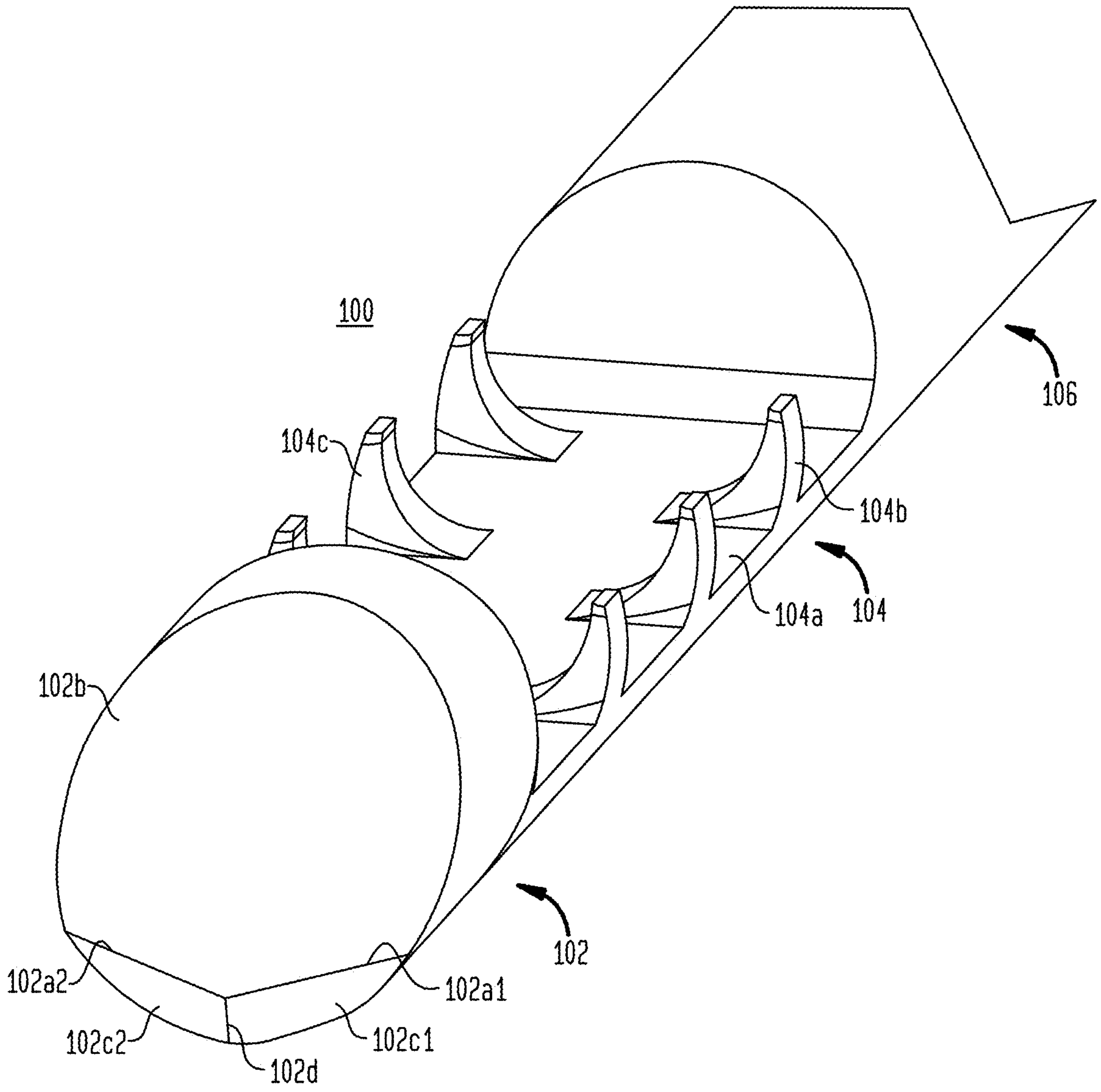
FIG. 4 is a perspective view of a distal portion of a biopsy needle, from a viewpoint distal from and to the left of the needle, according to some embodiments.

FIG. 4 is a perspective view of a distal portion of biopsy needle 100, from a viewpoint distal from and to the left of the needle, according to some embodiments. The most distal of teeth 104*c* is not visible in FIG. 4. Cutting edge 102*a* has a left portion 102*a*1 and a right portion 102*a*2 formed at the convergence of upper facet 102*b* with a left lower facet 102*c*1 and a right lower facet 102*c*2. Lower facets 102*c* and 102*c*2 converge at an edge 102*d* and all three facets meet at a point 102*c*. In top view of needle 100, cutting edge 102*a* is V-shaped. As seen in FIG. 2, the angle alpha of upper facet 102*b* to central axis A is less than the angle beta of lower facets 102*b* to central axis A.

Figure 5A:
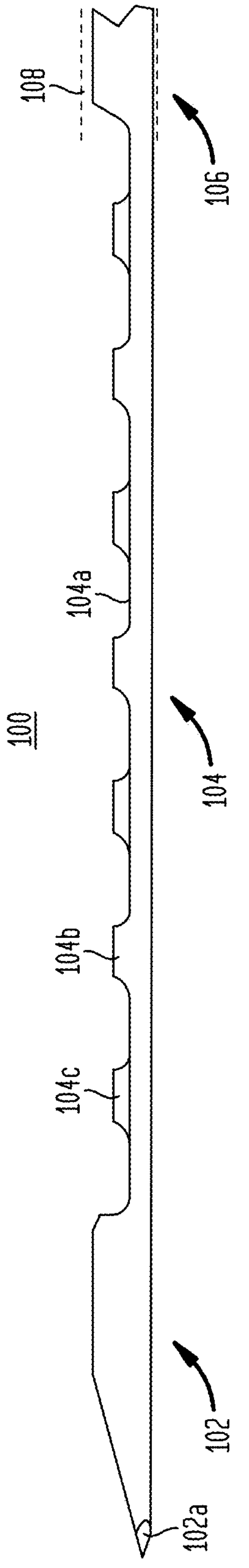
FIG. 5A is a left side view of a portion of a biopsy needle according to some embodiments and FIG. 5B is a comparable view of a portion of a prior art standard-of-care biopsy needle.
Figure 5B:
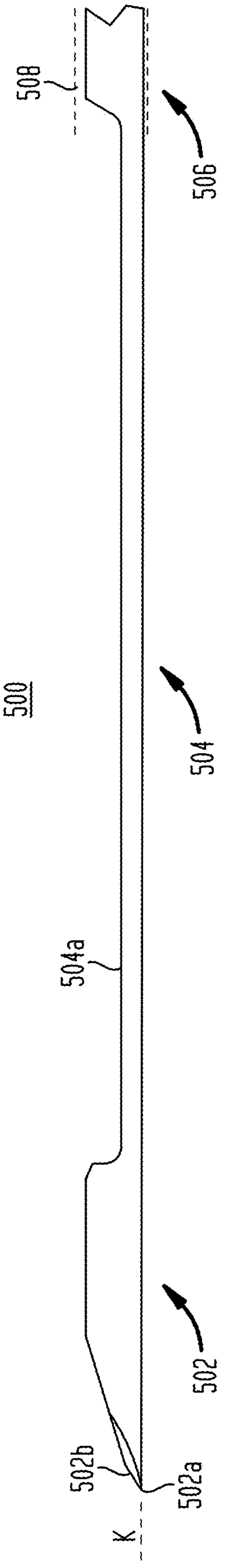
FIG. 5B (PRIOR ART)

FIG. 5A is a left side view of a portion of a biopsy needle 100 and FIG. 5B is a comparable view of a portion of a prior art standard-of-care biopsy needle 500. In each case, the biopsy needle typically is a part of a needle set that further includes a cutting cannula. Cutting cannula 108 is schematically shown in FIG. 5A and a like cutting cannula 508 is schematically shown in FIG. 5B. One important difference is that the standard-of-care biopsy needle 500 has no teeth in its notch 504*a* while needle 100 has teeth 104*b* and 104*c*. Another important difference is that the standard-of-care needle 500 terminates distally in a point 502*a* that is at the level K of the bottom of needle 500 while needle 100 terminates distally in a laterally extending edge 102*a* (not at a point) that is spaced up from the level B of the bottom extent of needle 100 and comprises edge portions 102*a*1 and 102*a*2.

Figure 6A:
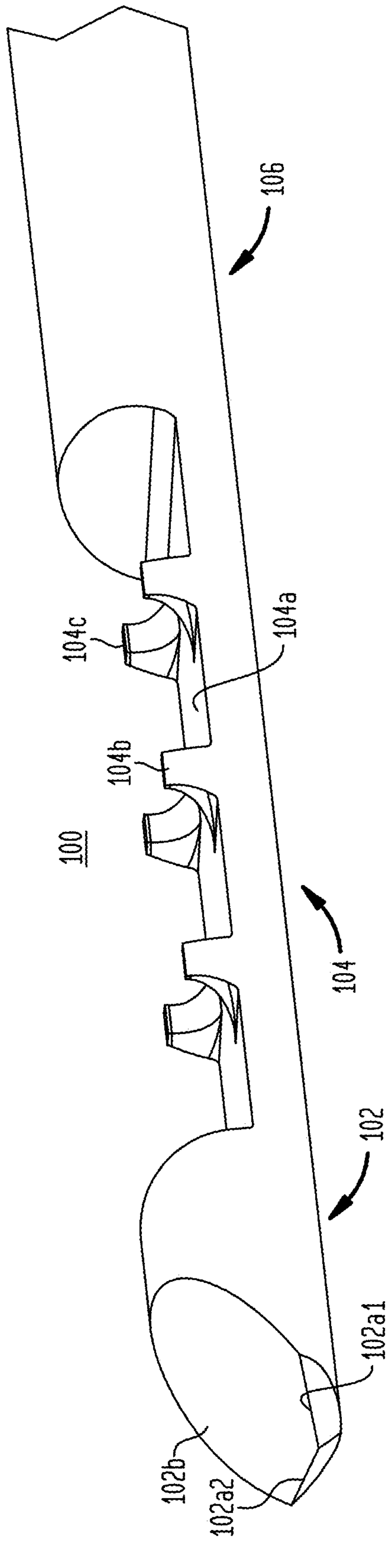
FIG. 6A is a perspective view of a left side of a portion of a biopsy needle according to some embodiments and FIG. 6B is a comparable perspective view of a portion of a prior art standard-of-care biopsy needle.
Figure 6B:
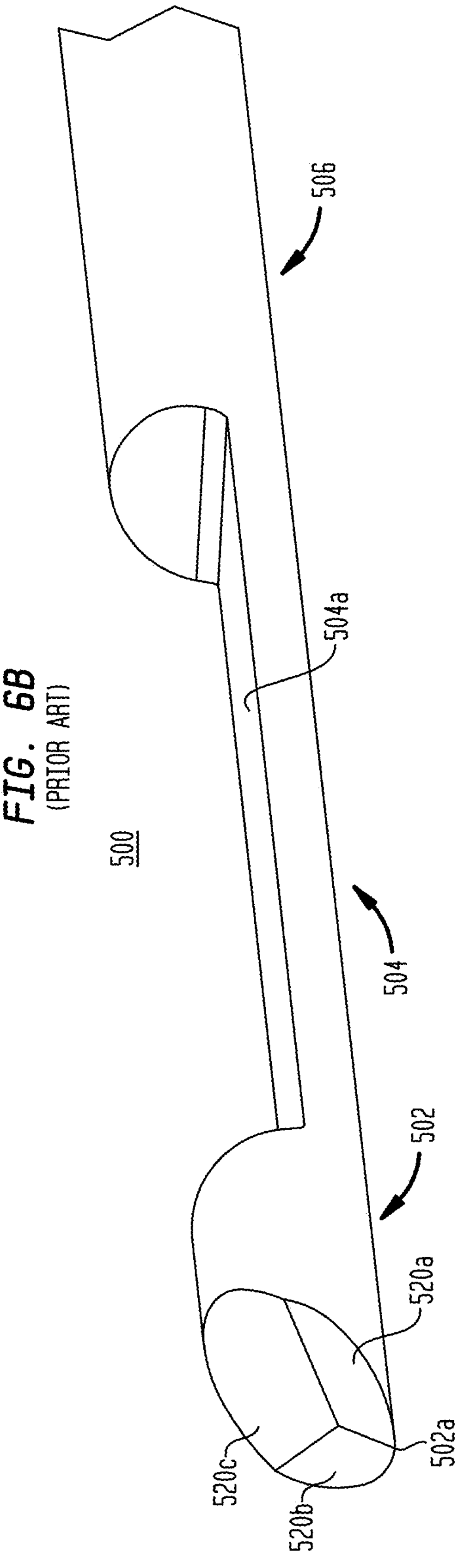
FIG. 6B (PRIOR ART)

FIGS. 6A and 6B are otherwise like FIGS. 5A and 5B, respectively, but show the respective biopsy needles from a point of view that is distal from and to the left of the needle tips 102 and 502. FIG. 6B shows that the needle tip terminates distally at a point where side facets 502*a* and 502*b* meet upper facet 502*c*. In contrast, as seen in FIG. 6A, tip 102 terminates distally in laterally extending edge 102*a* (comprising edges 102*a*1 and 1021*a*2) that is not a point. FIGS. 6A and 6B also show that cutting edge 102*a* is raised from the bottom extent of needle 100 while point 502*a* is at the level of the bottom extend of needle 500.

These differences have important consequences for the intended use of the biopsy needle sets, as discussed below regarding their typical use.

Biopsy needle sets such as seen in FIGS. 5A, 5B, 6A, and 6B typically are used as a part of a biopsy instrument with which a health professional takes tissue samples to observe for indications of conditions such as presence and nature of malignant cells. These instruments can be manual, or semi-automated, or fully automated. A manual instrument is discussed in U.S. Pat. No. 3,447,423, incorporated herein by reference. A biopsy needle such as needle 500 (but possibly with a differently shaped distal end) is fixedly mounded to and extends distally from a handle, and a cutting cannula such as cannula 508 is mounted in the handle to slide distally and proximally surrounding the needle. The health professional manually inserts the needle distally in patient tissue until its notched portion 504 in in the tissue of interest, and then manually pushes cannula 508 distally to sever tissue that has protruded into notch 504. The health professional then withdraws the needle and cannula from the patient and pulls the cannula proximally relative to the needle to uncover the tissue sample in the notch and remove it from the notch for assessment. A semi-automated biopsy instrument is discussed in U.S. Pat. No. 4,907,599, incorporated by reference herein. It differs from a manual instrument in that a spring-loaded cannula is released to shoot distally over the needle to sever tissue that has protruded into the needle notch. An automated instrument is illustrates as one mode of operation in U.S. Pat. No. 6,358,217 and differs in that both the needle and the cannula are spring-loaded, The health professional inserts into the patient the needle with the cutting cannula covering the needle notch until the distal end of the needle-cannula combination is near tissue of interest and then releases the spring-loaded needle to shoot distally such that its notch or cradle can enter the tissue of interest. After tissue has protruded into the notch or cradle, the spring-loaded cutting cannula shoots distally to sever a tissue sample.

Biopsy needle 100 and cutting cannula 108 have proximal ends (not shown) that can be secured to a biopsy instrument in a manner like that illustrated in said U.S. Pat. Nos. 3,447,423, 4,907,599 and 6,358,217, with suitable adaptations of the proximal ends or portions of the needle and cannula.

A goal in tissue biopsy medical procedures is to remove from the patient a tissue sample that is as large as possible given the size of the biopsy needle and cannula and as intact as possible, i.e., close in shape and nature to the way the tissue sample was in live tissue. Said parent patent application Ser. No. 17/082,387 (scheduled to issue as U.S. Pat. No. 11,903,569) and Ser. No. 18/119,042 (both incorporated by reference herein) describe biopsy needles provided with cradles formed by a cradle floor from the sides of which two rows of teeth extend up and discuss benefits of such needle configurations. These benefits include improved targeting of tissue of interest by helping the needle stay centered in the cannula and improved size and integrity of the tissue sample in medical procedures using biopsy instruments.

The needle tip 102 and cradle 104 described in this patent specification, using a laterally extending cutting edge 102*a* that is raised from the level of the bottom extent of the needle, further contribute to improved targeting and tissue sample quality.

Figure 7:
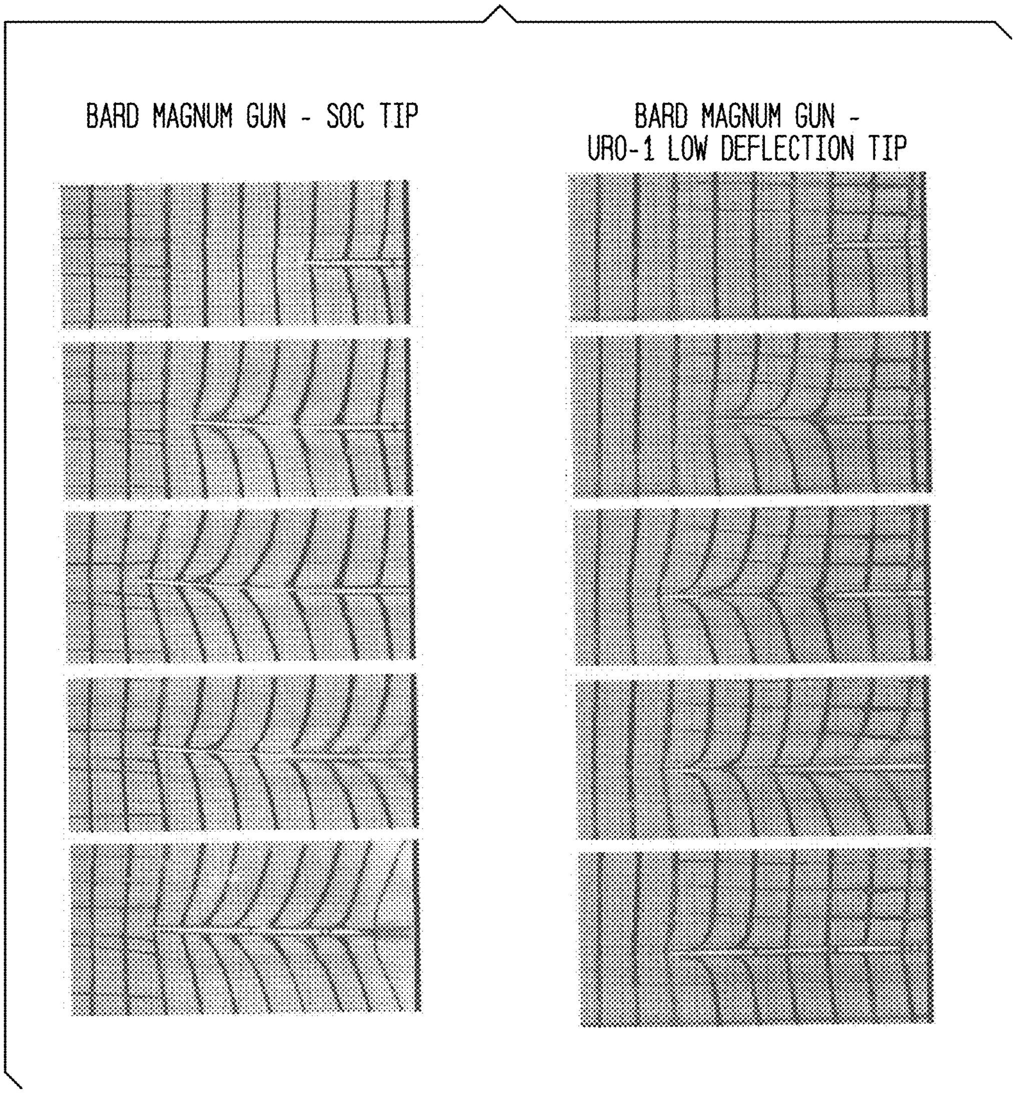
FIG. 7 illustrates a comparison of using a standard-of-care (SOC) biopsy needle set and a needle set using a biopsy needle described in this patent specification, according to some embodiments.

FIG. 7 illustrates a comparison of using a standard-of-care (SOC) biopsy needle set with a needle notched like that of FIGS. 5A and 5B and a needle set using biopsy needle 100 described in this patent specification. The images show penetration of a needle set in ballistic gel in which regularly spaced vertical lines of dye injected in the gel. In each case, the needle set is mounted to a well-known biopsy instrument—Bard Magnum Gun with a spring-loaded needle and cutting cannula. The dark up-down lines are the dye and initially are close to vertical. The top panel of each column of images shows an initial phase of penetrating the gel with a biopsy needle and a cutting cannula surrounding the needle notch (in the images in the left-hand column) and the cradle in the images in the right-hand column. As normally done when using semi-automatic and automatic biopsy instruments, in this phase the cutting cannula covers the notch or cradle in the biopsy needle. The top left image shows penetration using the SOC needle set and the top right image shows penetration with a needle 100 and cannula 108. A seen, the dye lines are displaced some more in the left image, indicating that tissue would be displaced and disturbed more when using the SOC needle set. The images in the second row from the top show a greater difference in performance in the phase when the needle is being shot distally relative to the cannula. With the SOC needle set, the needle starts to bend upward but needle 100 does not have such an upward bend, indicating better targeting. The third and fourth rows of images from the top show more dramatic differences—the SOC needle is bent much more, indicating poor targeting of tissue of interest, but needle 100 follows a straight path. The bottom row of images shows a phase in which the cutting cannula has shot distally over the tissue notch or cradle. The difference is very significant—the gel is much more disturbed and displaced with the SOC needle set than with the set of needles 100 and cannula 108. Some of the reasons for this difference may be that driving the cannula over the bent needle in the SOC set pulls gel downward from its initial position. This does not occur with needle 100 because it did not undergo such bending so driving cannula 108 over needle 100 did not pull gel down of otherwise cause gel displacement like in the left side images, Better targeting of needle 100 is due in part to the configuration of cradle 104 with its teeth 104*b* and 104*c* relative to cannula 108. As described in detail regarding like structures in said parent patent applications incorporated by reference, the lower surface of cradle 104 and the outer surface of the teeth that extend up from the cradle floor bear against the inside surface of cannula 108 as cradle 104 moves distally out of cannula 108 into tissue of interest to thereby keep the portion of needle 100 that project distally from cannula 108 straighter and to keep the portion of cradle 104 that is inside cannula 108 centered in the cannula.

Further improvement in targeting is believed due to shaping the distal end of tip 102 as a laterally extending cutting edge 102*a* rather than as a point like in the SOC needle of FIGS. 5B and 6B. Experiments such as illustrated in FIG. 7 and with tissue indicate better targeting that is believed facilitated by less vertical displacement of tissue as needle 100 moves distally into tissue compared with a needle tip such as in FIGS. 5B and 6B where the cutting point is at the level of the bottom of the needle and the upper facet starts at that point.

Better quality tissue samples are obtained with needle having a cradle like cradle 104 compared with the SOC needle with an open notch as described in detail in said parent applications incorporated by reference. Declarations of experts submitted in said parent application Ser. No. 17/082,387 (scheduled to issue as U.S. Pat. No. 11,903,569) confirm that in patient trials the needle with teeth performed significantly and unexpectedly better than the SOC needle with an open notch. The better performance includes obtaining tissue samples that have greater cross-sections, more volume, and less distortion such as stretching, breading up, or bunching compared to the SOC needle.

Although the foregoing describes embodiments in some detail for purposes of clarity, it will be apparent that certain changes and modifications may be made without departing from the principles thereof. There can be alternative ways of implementing both the processes and apparatuses described herein. As a non-limiting example, the distal cutting edge 102*a* may be shaped such that it is not V-shaped in a top view but is straight or has another shape in a top view, such as a laterally extending straight line or curved line. Accordingly, the present embodiments are to be considered as illustrative and not restrictive, and the body of work described herein is not to be limited to the details given herein, which may be modified within the scope and equivalents of the appended claims.

The invention claimed is:

1. A biopsy needle set comprising:

a biopsy needle that extends along a central axis that is at a level midway between a top extent and a bottom extent of the needle, wherein said needle comprises:

a tip, a cradle proximal to the tip, and a shaft proximal to the cradle, wherein:

the tip comprises upper and lower facets that converge to each other in a distal direction to form a distal cutting edge that is at the distal end of the tip and extends in a lateral direction;

the cradle comprises an upwardly facing floor that is between said central axis and the bottom extent of the needle, has lateral sides flanking the central axis, and a row of individual teeth that extend up from each lateral side of said floor to a level approximating that of the central axis, wherein the individual teeth of each row are spaced from each other along the central axis, such that a gap is formed between each of the individual teeth of each row; and said laterally extending, distal cutting edge is spaced up from said bottom extent of the needle but is below the level of said floor of the cradle such that the facets converge only at or below the cutting edge that is below the cradle floor that in turn is below the central axis;

wherein as the needle shoots into tissue, the needle tip portion that is below the cutting edge limits vertical displacement of tissue facilitates improved targeting when compared with needles in which the point distal edge is at a bottom end of a needle, and wherein having the cutting edge below the cradle floor facilitates collecting in the cradle a tissue sample that maintains better integrity when compared with needles in which edges radiate from a point tip at a central axis of the needle.

2. The biopsy needle set of claim 1, in which said distal cutting edge is at a level spaced up from the bottom extent of the needle by a distance approximating a third of the distance from the bottom extent of the needle to the level of the floor of the cradle.

3. The biopsy needle set of claim 1, in which said distal cutting edge is at a level spaced up from the bottom extent of the needle by 15 thousandths of an inch plus or minus 5 thousandth of an inch.

4. The biopsy needle set of claim 1, in which said upper and lower facets comprise two lower facets and that are side-by-side.

5. The biopsy needle set of claim 1, in which said lower facets comprise two lower facets that converge to an up-down edge that is below and extends proximally from the laterally extending cutting edge.

6. The biopsy needle set of claim 1, in which said upper and lower facets comprise two lower facets each of which is shorter along the central axis than the upper facet.

7. The biopsy needle set of claim 1, in which the teeth are arranged such that some cross-sections of the cradle include only one of said teeth and some do not include any of said teeth.

8. The biopsy needle set of claim 1, in which said laterally extending distal cutting edge is V-shaped in top view.

9. The biopsy needle set of claim 1, in which said laterally extending distal cutting edge comprises two portions each extending along a respective straight line.

10. The biopsy needle set of claim 1, in which said laterally extending distal cutting edge extends along a single straight line.

11. The biopsy needle set of claim 1, in which said laterally extending distal cutting edge extends along at least one curved line.

12. The biopsy needle set of claim 1, further comprising a hollow cutting cannula configured to slide distally and proximally over the biopsy needle along the central axis such that an outside bottom surface of the cradle and outside surface of the teeth bear against an inner surface of the cannula to keep the needle centered in the cannula to resist bending of the needle when a part of the cradle extends distally out of the cannula.

13. A biopsy needle set comprising a biopsy needle that extends along a central axis that is at a level midway between a top extent and a bottom extent of the needle, wherein said needle comprises:

a tip, a cradle proximal to the tip, and a shaft proximal to the cradle, wherein:

the tip comprises one upper and a plurality of lower facets that converge to each other to form a distal cutting edge that:

is at the distal end of the tip extends in a lateral direction, and is at an intersection of the upper facet with the plurality of lower facets;

wherein the cradle comprises an upwardly facing floor that is between said central axis and the bottom extent of the needle, has lateral sides flanking the central axis, and a row of individual teeth that extend up from each lateral side of said floor to a level approximating that of the central axis, wherein the individual teeth of each row are spaced from each other along the central axis, such that a gap is formed between each of the individual teeth of each row; and said laterally extending, distal cutting edge is spaced up from said bottom extent of the needle but is below the level of said floor of the cradle such that the facets converge only at or below the cutting edge that is below the cradle floor that in turn is below the central axis;

wherein as the needle shoots into tissue, the needle tip portion that is below the cutting edge limits vertical displacement of tissue facilitates improved targeting when compared with needles in which the point distal edge is at a bottom end of a needle, and wherein having the cutting edge below the cradle floor facilitates collecting in the cradle a tissue sample that maintains better integrity when compared with needles in which edges radiate from a point tip at a central axis of the needle.

14. The biopsy needle set of claim 13, in which the plurality of lower facets that are angled to each other.

15. The biopsy needle set of claim 13, in which the cutting edge is along a laterally extending straight line at which the needle terminates distally.

16. The biopsy needle of claim 13, in which the cutting edge is along a laterally extending curved line at which the needle terminates distally.

* * * * *